US00PP30325P2

(12) United States Plant Patent
Cain

(10) Patent No.: US PP30,325 P2
(45) Date of Patent: Apr. 2, 2019

(54) GRAPEVINE PLANT 'IFG THIRTY-FOUR'

(50) Latin Name: ***Vitis interspecific* hybrid**
Varietal Denomination: IFG Thirty-four

(71) Applicant: David Cain, Bakersfield, CA (US)

(72) Inventor: David Cain, Bakersfield, CA (US)

(73) Assignee: INTERNATIONAL FRUIT GENETICS, LLC, Bakersfield, CA (US)

( * ) Notice: Subject to any disclaimer, the term of this patent is extended or adjusted under 35 U.S.C. 154(b) by 0 days.

(21) Appl. No.: 15/732,705

(22) Filed: Dec. 18, 2017

(51) Int. Cl.
*A01H 5/08* (2018.01)

(52) U.S. Cl.
USPC ..... Plt./205
CPC ..... *A01H 5/08* (2013.01)

(58) Field of Classification Search
USPC ..... Plt./205
CPC ..... A01H 5/0812
See application file for complete search history.

*Primary Examiner* — Kent L Bell

(57) ABSTRACT

This invention is a new and distinct grapevine variety denominated 'IFG Thirty-four'. The new grapevine plant is characterized by producing small naturally seedless reddish black to black berries having round shape with a strong concord-like labrusca flavor. Fruits are medium in acidity, with a very soft juicy texture and have excellent eating quality.

1 Drawing Sheet

Latin name of the genus and species claimed: *Vitis interspecific* hybrid.

Variety denomination: 'IFG Thirty-four'.

BACKGROUND OF THE INVENTION

The new and distinct grapevine plant described and claimed herein originated from a hand pollinated cross of A2304 and 01114 bulk (a bulked pollen composed of two unnamed sibling *Vitis interspecific* hybrid selections from the IFG breeding program) hybridized in May 2004. The abortive seed traces were subsequently embryo cultured and the resulting 124 plants were planted in the field in April 2005. The present variety of grapevine was selected as a single plant in July 2006 and was first asexually propagated by hardwood cuttings in December 2006 near Delano, Kern County, Calif. The resulting propagules were planted during April 2007 near Delano, Kern County, Calif. and were found to reproduce true-to-type through at least one generation of asexual reproduction.

BRIEF SUMMARY OF THE INVENTION

The new grapevine 'IFG Thirty-four' is characterized by producing small naturally seedless reddish black to black berries having round shape with a strong concord-like labrusca flavor. Fruits are medium in acidity, with a very soft juicy texture and have excellent eating quality. Berries color readily even in hot climatic conditions and produce completely colored reddish black to black berries. Vines are productive and can be pruned to short spurs. Clusters are medium size, and often do not set enough berries which can be ameliorated by tipping before bloom. Berry size can be increased by applying gibberellic acid. The new grapevine plant differs from its maternal parent A2304 by having reddish black to black berry color with a round shape and small residual seed trace as opposed to the elongated white berries with large seed traces of A2304. 'IFG Thirty-four' ripens approximately one month before A2304. 'IFG Thirty-four' can be distinguished from either of its pollen parents in 01114 bulk, by having much larger cluster size than either of the 01114 siblings and by having a more black color as opposed to the more red color of the siblings.

'IFG Thirty-four' is most similar to the Tomcord (non-patented) variety. It differs from 'Tomcord' by ripening earlier, by having larger berry size, by having smaller residual seed traces, and by having a looser more open cluster density.

'IFG Thirty-four' is also somewhat similar to 'Concord Seedless' but can be distinguished by having larger, looser clusters with larger berry size and smaller seed traces than 'Concord Seedless'.

Grape breeders have used several native American grape species to improve hardiness, disease and insect resistance as well as incorporate aromatic flavors into the vinifera species. Previously introduced interspecific varieties have had very limited commercial success due to small fruit size, large seed traces, and slipskin texture. The new grapevine variety is being introduced because of its excellent concord-like flavor combined with seedlessness, and good adhesion of skin and flesh.

BRIEF DESCRIPTION OF THE DRAWING

The accompanying photographic drawing in FIG. 1 illustrates in full color 'IFG Thirty-four', taken from a 4-year-old vine.

The photograph was taken outdoors with indirect lighting. The colors are as nearly true as is reasonably possible in a color representation of this type. The left side of the drawing has a mature leaf and a typical berry in cross-section. A mature fruit cluster is represented in the center of the drawing. A young shoot with tendrils can be seen on the right side of the drawing

DETAILED BOTANICAL DESCRIPTION OF THE INVENTION

Throughout this specification, color names beginning with a small letter signify that the name of that color, as used in common speech, is aptly descriptive. Color names beginning with a capital letter designate values based upon R.H.S. Colour Chart, published in 2001 by The Royal Horticultural Society, London, England.

Throughout this specification subjective description values conform to those set forth by the International Plant Genetic Resources Institute publication 'Descriptors for Grape' (*vitis* spp.) (1983) which was developed in collaboration with the Office International de la Vigne et du Vin (OIV) and the International Union for the Protection of New Varieties of Plants (UPOV).

The descriptive matter which follows pertains to 'IFG Thirty-four' 4-year-old plants grown in the vicinity of Delano, Kern County, Calif. during 2013 and 2014, and is believed to apply to plants of the variety grown under similar conditions of soil and climate elsewhere:

VINE

General:

*Vigor*.—Vigorous.

*Density of foliage*.—Dense.

*Productivity*.—Medium productive, producing about 17.7 to 26.5 kg of fruit per vine.

*Root stock*.—Own root.

*Training method*.—Typically spur pruned leaving 2 bud spurs.

Trunk:

*Trunk diameter of* 4-*year-old vines at* 30 *cm above the soil line*.—About 3.9 cm.

*Shape*.—Medium slender.

*Straps*.—Long, continuous.

*Surface texture*.—Medium to somewhat rough.

*Inner bark color*.—The following colors were observed: Greyed Orange: 177A and 177B and 166B.

*Outer bark color*.—Greyed-brown: 199B.

SHOOTS

Young shoot:

*Form of tip*.—Fully opened.

*Distribution of anthocyanin coloration of tip*.—Absent.

*Intensity of anthocyanin coloration of tip*.—Absent.

*Density of prostrate hairs of tip*.—Medium.

*Density of erect hairs of tip*.—Absent.

*Color*.—Yellow-green: N144 A.

Woody shoot (mature canes):

*Internode length*.—Long: About 17.2 cm.

*Width at node*.—About 1.3 cm.

*Cross section*.—Elliptic.

*Surface*.—Striate.

*Main color*.—The following colors were observed: Greyed-orange: 165A and 166A and 166B.

*Density of erect hairs of nodes*.—None.

*Density of erect hairs on internodes*.—None.

*Growth of axillary shoots*.—Weak: Approximately 4.2 cm.

Flowering shoot:

*Vigor during flowering*.—Strong.

*Attitude during flowering on shoots not tied*.—Semi-erect.

*Color*.—Dorsal side of internodes Yellow-green: 146C.

*Color*.—Ventral side of internodes — Yellow-green: 146C.

*Color*.—Dorsal side of nodes — Yellow-green: 146C.

*Color*.—Ventral side of nodes — Yellow-green: 146C.

*Density of prostrate hairs of nodes*.—Very sparse.

*Density of erect hairs of nodes*.—None to very sparse.

*Density of prostrate hairs on internode*.—Very sparse.

*Density of erect hairs on internode*.—None.

*Anthocyanin coloration of buds*.—Absent.

Tendrils: (at full bloom):

*Distribution on the shoot* (*at full flowering*).—Discontinuous.

*Length of tendril*.—Long: About 30 cm.

*Thickness of tendril* 2 *cm from base*.—About 2.6 mm.

*Color*.—Yellow-green: N144A.

*Form*.—Mixture of bifurcated and trifurcated.

*Number of consecutive tendrils*.—2.

LEAVES

Young leaves:

*Color of upper surface of first four distal unfolded leaves*.—Yellow-green: 144A.

*Color of lower surface of young leaves*.—Yellow-green: 144A.

*Average intensity and color of anthocyanin coloration of six distal leaves prior to flowering*.—Absent or very weak.—Red-purple: 59B.

*Density of prostrate hairs between veins* (*lower surface*).—Absent to very sparse.

*Density of prostrate hairs on veins* (*lower surface*).—Sparse.

*Density of erect hairs between veins* (*lower surface*).—Absent.

*Density of erect hairs on veins* (*lower surface*).—Very sparse to sparse.

Mature leaves:

*Average length*.—About 11.0 cm.

*Average width*.—About 14.4 cm.

*Mature leaf size*.—Small to medium.

*Shape of blade*.—Wedge shaped.

*Number of lobes*.—5.

*Blade venation*.—Palmate.

*Anthocyanin coloration of main veins on upper side of blade*.—Absent.

*Mature leaf profile*.—Flat.

*Blistering surface of blade upper surface*.—Absent to very weak.

*Leaf blade tip*.—In the plane of the leaf.

*Leaf apex*.—Acute.

*Leaf margin*.—Serrate.

*Undulation of margin*.—Slight.

*Thickness*.—Medium.

*Undulation of blade between main and lateral veins*.—Absent.

*Shape of teeth*.—Mixture of both sides straight and both sides convex.

*Length of teeth*.—Long.

*Ratio length/width of teeth*.—Large.

*Shape of upper lateral sinuses*.—Closed to lobes slightly overlapping.

*Depth of upper lateral sinuses*.—Medium to deep.

*General shape petiole sinus*.—Closed to lobes slightly overlapping.

*Shape of base of upper leaf sinuses*.—V-shaped.

*Tooth at petiole sinus*.—Absent.

*Density of prostrate hairs between veins on lower surface of blade*.—Very sparse.

*Density of erect hairs between veins on lower surface of blade*.—Absent.
*Density of prostrate hairs on main veins on lower surface of blade*.—Sparse.
*Density of erect hairs on main veins on lower surface of blade*.—Sparse.
*Density of prostrate hairs on main veins on upper surface of blade*.—Very sparse.
*Density of erect hairs on main veins on upper surface of blade*.—None.
*Autumn coloration of leaves*.—Leaves can be a single color or combination of colors, in a mottled pattern or on the edges of the leaves. The following colors were observed: Greyed-yellow: 162A and 162B, Greyed-purple:187A and 187B.

Upper surface:
*Color*.—The following colors were observed: Green: 137A and 137B.
*Anthocyanin coloration of main veins*.—Absent.
*Color of main veins*.—Yellow-green: 144C.
*Surface appearance*.—Semi-glossy to dull.
*Blistering surface of blade*.—Very weak.

Lower surface:
*Color*.—The following colors were observed: Yellow green: 146A and 146B.
*Anthocyanin coloration of main veins* (*lower surface*).—Absent.
*Color of main veins*.—Yellow-green: 145C.
*Glossiness*.—Weak.
*Surface texture*.—Smooth.
*Surface appearance*.—Semi-glossy to dull.

Petiole:
*Length*.—About 9 cm.
*Diameter of petiole 2 cm from blade*.—About 3.2 mm.
*Petiole color*.—Yellow-green: 145A.
*Length of petiole compared to middle vein*.—Slightly shorter.
*Density of prostrate hairs on petiole*.—Very sparse.
*Density of erect hairs on petiole*.—Very sparse.

Buds:
*Bud fruitfulness*.—Basal: Mostly fruitful.
*Position of first fruitful shoot on previous season cane*.—$1^{st}$ to $2^{nd}$ node.
*Dormant bud length*.—About 4.6 mm.
*Dormant bud width in the proximal/distal plane*.—About 6.2 mm.
*Dormant bud color*.—Greyed-orange: 166A.
*Time of bud burst*.—Medium to late: Mar. 5, 2014.

FLOWERS

General:
*Flower sex*.—Hermaphrodite.
*Length of single flower, unopened*.—About 3.0 mm.
*Width of single flower*.—Unopened: About 2.0 mm. Opened: About 6.2 mm.
*Stamen length*.—About 3.1 mm.
*Stamen count*.—5.
*Pollen color*.—Yellow: 10C.
*Pistil length*.—About 2.5 mm.
*Pistil color*.—Yellow-green: 144B.
*Length of first inflorescence*.—Medium long: About 23.6 cm long by 11.6 cm wide.
*Position of first flowering and fruiting node*.—$4^{th}$ (current season growth).
*Number of inflorescence per flowering shoot*.—1.1 to 2: About 1.9.
*Time of bloom*.—Early as compared with similar varieties in the growing area of Delano, Calif.
*Date of full bloom*.—Apr. 25, 2014.

FRUIT

General:
*Ripening period*.—Early: Approximately Jul. 18, 2014.
*Use*.—Fresh market.
*Keeping quality*.—Good.
*Resistance to*.—Insects: Average typical of *Vitis vinifera* species. Diseases: Average typical of *Vitis vinifera* species.
*Refractometer test*.—Solid-sugar: About 22.8 Brix.
*Brix/acid*.—About 51.8.
*Titratable acidity*.—About 0.44.
*Juice ph*.—About 3.78.

Cluster:
*Mature cluster length* (*peduncle excluded*).—About 30.9 cm.
*Mature cluster width*.—About 14.2 cm.
*Mature cluster weight*.—About 589 g.
*Bunch density*.—Medium to overly sparse.
*Number of berries*.—About 153.
*Form*.—Conical.

Peduncle:
*Lignification of peduncle*.—Weak.
*Diameter of peduncle*.—About 4.8 mm.
*Length of peduncle*.—Medium: Approximately 5.5 cm.
*Color of peduncle*.—Yellow-green: 144C.

Berry:
*Uniformity of size*.—Uniform to slightly variable.
*Single berry weight*.—About 4.6 g natural: to about 5.8 g when treated with gibberellic acid.
*Shape*.—Round.
*Seeds*.—Absent.
*Cross section*.—Circular.
*Berry dimensions*.—Longitudinal axis: About 2.0 cm. horizontal axis: About 1.9 cm.
*Pedicel length*.—About 7.3 mm.
*Pedicel width*.—About 2.2 mm.
*Pedicel color*.—Yellow-green: 144D.
*Berry firmness*.—Soft.
*Particular flavor*.—Labrusca.
*Bloom* (*cuticular wax*).—Strong.
*Berry separation from pedicel*.—Medium.
*Skin color* (*without bloom*).—Greyed-purple: N186A.
*Flesh color*.—Yellow-green: 145D.

Skin:
*Thickness*.—Medium.
*Skin toughness*.—Somewhat notable when chewing.
*Reticulation*.—Absent.
*Tenacity*.—Tenacious to flesh.

What is claimed:

1. A new and distinct variety of grapevine plant as herein illustrated and described.

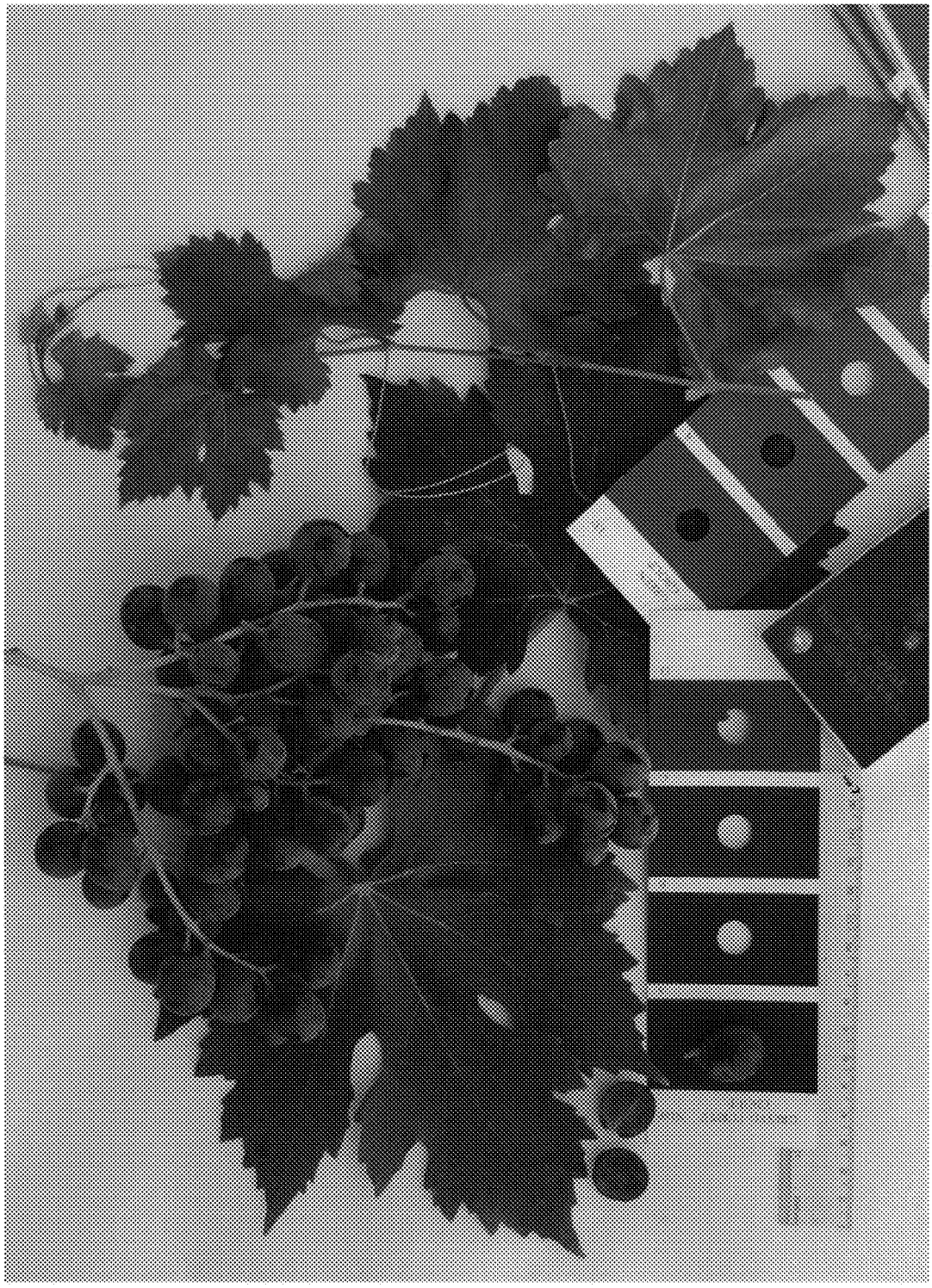

* * * * *